United States Patent
Lerebour et al.

(10) Patent No.: US 11,607,374 B2
(45) Date of Patent: Mar. 21, 2023

(54) OIL-IN-WATER EMULSION COMPRISING A SPECIFIC SURFACTANT SYSTEM

(71) Applicant: L'OREAL, Paris (FR)

(72) Inventors: Geraldine Lerebour, Chevilly la Rue (FR); Charlotte Lemaire, Chevilly la Rue (FR); Franck Clement, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/471,287

(22) PCT Filed: Dec. 8, 2017

(86) PCT No.: PCT/EP2017/082088
§ 371 (c)(1),
(2) Date: Jun. 19, 2019

(87) PCT Pub. No.: WO2018/114406
PCT Pub. Date: Jun. 28, 2018

(65) Prior Publication Data
US 2020/0085702 A1    Mar. 19, 2020

(30) Foreign Application Priority Data

Dec. 22, 2016 (FR) ..................... 1663271

(51) Int. Cl.
| | | |
|---|---|---|
| A61K 8/06 | (2006.01) | |
| A61K 8/37 | (2006.01) | |
| A61K 8/46 | (2006.01) | |
| A61K 8/73 | (2006.01) | |
| A61K 8/92 | (2006.01) | |
| A61Q 19/00 | (2006.01) | |

(52) U.S. Cl.
CPC .............. *A61K 8/062* (2013.01); *A61K 8/375* (2013.01); *A61K 8/463* (2013.01); *A61K 8/466* (2013.01); *A61K 8/733* (2013.01); *A61K 8/737* (2013.01); *A61K 8/922* (2013.01); *A61Q 19/00* (2013.01); *A61K 2800/412* (2013.01); *A61K 2800/436* (2013.01); *A61K 2800/596* (2013.01)

(58) Field of Classification Search
CPC ...................................... A61Q 19/00
See application file for complete search history.

(56) References Cited

U.S. PATENT DOCUMENTS

| | | | |
|---|---|---|---|
| 2005/0106190 A1 | 5/2005 | Kawa et al. | |
| 2015/0352016 A1* | 12/2015 | Shah | A61K 8/4993 424/59 |
| 2017/0014315 A1* | 1/2017 | Riedel | A61K 8/92 |

FOREIGN PATENT DOCUMENTS

| | | | |
|---|---|---|---|
| CN | 105960227 A | 9/2016 | |
| EP | 1 917 954 A1 | 5/2008 | |
| WO | WO 03/051960 A1 | 6/2003 | |
| WO | WO 2007/085568 A1 | 8/2007 | |
| WO | WO-2009003996 A1 * | 1/2009 | ............. A61Q 19/02 |
| WO | WO 2015/117841 A2 | 8/2015 | |

OTHER PUBLICATIONS

International Search Report dated Feb. 13, 2018 in PCT/EP2017/082088 filed Dec. 8, 2017.
Combined Chinese Office Action and Search Report dated Nov. 23, 2021 in Chinese Patent Application No. 201780086834.0 (with English translation of Categories of Cited Documents), citing document AO therein, 9 pages.

* cited by examiner

*Primary Examiner* — Gina C Justice
(74) *Attorney, Agent, or Firm* — Womble Bond Dickinson (US) LLP

(57) ABSTRACT

The invention relates to a cosmetic composition in the form of an oil-in-water emulsion comprising: (i) at least one lipophilic surfactant with HLB less than or equal to 9, and (ii) at least one specific anionic surfactant comprising at least one sulfate and/or sulfonate function; said composition comprising from 0% to 8% by weight of additional surfactant(s) relative to the total weight of the composition. It also relates to the associated cosmetic process.

17 Claims, No Drawings

OIL-IN-WATER EMULSION COMPRISING A SPECIFIC SURFACTANT SYSTEM

The invention relates to a cosmetic composition in the form of an oil-in-water emulsion comprising a lipophilic surfactant with HLB less than or equal to 9 and a specific anionic surfactant comprising at least one sulfate and/or sulfonate function.

The invention also relates to a cosmetic treatment process for keratin materials comprising the application of said composition.

Oil-in-water emulsions comprising a polyglycerol ester and fatty polyacids such as polyglyceryl-2 dipolyhydroxystearate as lipophilic surfactant and an alkylpolyglucoside such as lauryl glucoside as hydrophilic surfactant are known from documents WO02013076691 and EP 1 917 954. These emulsions have the particularity of undergoing phase inversion when they are applied to keratin materials. However, the combination of surfactants described in these two documents does not produce stable compositions in the sense of the present invention. Also, these compositions present a reduced duration of application or "playtime" because of too fast a phase inversion during application on the keratin materials, this reduction of the duration of application causes a difficulty in correctly spreading the composition on the skin and does not favour the production of an even deposit, particularly when the composition comprises pigments.

Additionally, oil-in-water emulsions having the property of phase inversion during application on keratin materials comprising a polyglycerol ester and fatty polyacids such as polyglyceryl-2 dipolyhydroxystearate as lipophilic surfactant and a surfactant comprising a sulfonate function such as disodium cetearyl sulfosuccinate as hydrophilic surfactant are also known from document WO02015117841. Nevertheless, the compositions described in this document also present a reduced duration of application or "playtime" as mentioned previously.

The present invention therefore aims to provide compositions in the form of oil-in-water emulsions exhibiting phase inversion upon application and exhibiting satisfactory duration of application on keratin materials, preferably skin.

Moreover, the present invention also aims to provide compositions in the form of oil-in-water emulsions exhibiting a phase inversion upon application, having good stability properties, in particular exhibiting better stability than with the lauryl glucoside and polyglyceryl-2 dipolyhydroxystearate combination as described in documents WO02013076691 and EP 1 917 954.

"Playtime" and "duration of application" are understood to mean the duration during which the composition remains sufficiently fluid to be applied to the keratin materials. A playtime is called satisfactory when the duration of application is between 45 and 75 seconds, preferably between 50 and 70 seconds, better still between 55 and 70 seconds, particularly as indicated in the examples hereinafter.

A composition is called stable when no or little change in its macroscopic and/or microscopic appearance and/or its physical and chemical characteristics (viscosity) is observed after storage at ambient temperature (25° C.) for a duration of one month, preferably 2 months and/or after storage at a temperature of 55° C. for a duration of 15 days.

The viscosity measurement is carried out at 25° C., using a Rheomat RM 180 viscometer equipped with a No. 3 spindle, the measurement being carried out after 10 minutes of rotation of the spindle in the composition (after which time stabilization of the viscosity and of the speed of rotation of the spindle are observed), at a shear rate of $200\ s^{-1}$.

The Applicant has discovered in a surprising manner that the combination of at least one specific anionic surfactant comprising at least one sulfate and/or sulfonate function, and at least one lipophilic surfactant with HLB less than or equal to 9, produces a composition in the form of an oil-in-water emulsion that undergoes phase inversion when applied to keratin materials, in particular to skin, and exhibits a satisfactory duration of application on keratin materials, preferably skin.

Moreover, the composition according to the invention exhibits good stability properties.

Additionally, the composition according to the invention also exhibits good cosmetic properties, particularly a sensation of freshness upon application and a lighter and less greasy feel after application.

Accordingly, the present invention relates to a cosmetic composition in the form of an oil-in-water emulsion comprising:
 (i) at least one lipophilic surfactant with HLB less than or equal to 9;
 (ii) at least one anionic surfactant comprising at least one sulfate and/or sulfonate function;
said anionic surfactant comprising at least one sulfonate function is chosen from (C6-C30)alkylsulfonates, (C6-C30)alkylamidesulfonates, (C6-C30)alkylarylsulfonates, alpha-olefin-sulfonates, paraffin-sulfonates, (C6-C30)alkylsulfoacetates, N-acyl(C6-C30)-N—(C1-C6)alkyltaurates, (C6-C30)acylisethionates, (C6-C30)alkylsulfolaurates, and mixtures thereof,
said composition comprising from 0% to 8% by weight of additional surfactant(s) relative to the total weight of the composition.

The composition according to the invention is intended for topical application and thus comprises a physiologically acceptable medium. The term "physiologically acceptable medium" is intended to mean a medium that is compatible with human keratin tissues such as the skin, mucous membranes and the scalp.

The present invention also relates to a cosmetic treatment process for keratin materials, characterized in that a composition in accordance with the present invention is applied to said keratin materials, particularly to skin and in particular the skin of the face and/or body.

In the present description, the expression "at least one" is equivalent to "one or more" and, unless otherwise indicated, the limits of a range of values are comprised in that range.

Phase Inversion Technology

The composition oil-in-water emulsion according to the invention exhibits the property of phase inversion when applied to keratin materials because of the shear generated when it is spread with the fingers, using a sponge, or with a brush, preferably with the fingers, in other words due to the mechanical energy caused by the user's gestures upon application.

With the phase inversion that occurs when the composition according to the present invention is applied to keratin materials, preferably to skin, a lipophilic film is obtained on the skin more quickly in comparison with application of an oil-in-water composition with simple evaporation of the aqueous phase without phase inversion.

Also, the oil-in-water emulsion according to the invention exhibits, during the application to skin, good penetration properties, a feeling of freshness, and a less greasy, less sticky and lighter finish after application.

Combination of at Least One Anionic Surfactant and at Least One Lipophilic Surfactant Anionic Surfactant The composition according to the invention comprises at least one anionic surfactant comprising at least one sulfate and/or sulfonate function.

Advantageously said anionic surfactant has an HLB greater than or equal to 13. The HLB value according to Griffin is defined in J. Soc. Cosm. Chem. 1954 (volume 5), pages 249-256.

Reference may be made to the document "Encyclopedia of Chemical Technology, Kirk-Othmer", volume 22, pp. 333-432, 3rd edition, 1979, Wiley, for the definition of the properties and (emulsifying) functions of surfactants, in particular pp. 347-377 of this reference, for anionic, amphoteric and non-ionic surfactants.

The anionic surfactants comprising at least one sulfonate ($-SO_3H$ or $-SO_3^-$) function are chosen from the following compounds, alone or in mixtures: alkylsulfonates, alkylamidesulfonates, alkylarylsulfonates, alpha-olefin-sulfonates, paraffin-sulfonates, alkylsulfoacetates, acylisethionates, alkylsulfolaurates, and the salts of these compounds, the alkyl or acyl groups of these compounds including from 6 to 30 carbon atoms, in particular from 6 to 20, better still from 8 to 16, or 10 to 14 carbon atoms, the aryl group preferably denoting a phenyl or benzyl group; N-acyl-N-alkyltaurates, and the salts of these compounds, the alkyl group of these compounds including from 1 to 6 carbon atoms and the acyl group including from 6 to 30 carbon atoms, in particular from 6 to 20, better still from 8 to 16, or from 10 to 14 carbon atoms;

these compounds possibly being polyoxyethylenated and then preferably including from 1 to 50 ethylene oxide units and better still from 2 to 10 ethylene oxide units.

In a specific embodiment, the acyl group of said anionic surfactants comprising at least one sulfonate function is derived from a mixture of C6-C24, preferably C6-C20, better still C8-C16, or C10-C14 fatty acids.

Preferably, the anionic surfactant comprising at least one sulfonate function is chosen from:

acylisethionates, the linear or branched acyl group comprising from 6 to 24 carbon atoms, preferably from 6 to 20 carbon atoms, preferentially from 8 to 16 carbon atoms and better still from 10 to 14 carbon atoms;

N-acyl-N-alkyltaurates, the linear or branched acyl group comprising from 6 to 24 carbon atoms, preferably from 6 to 20 carbon atoms, better still from 8 to 16, or from 10 to 14 carbon atoms, and the linear or branched alkyl group comprising from 1 to 6 carbon atoms, or cyclic group comprising from 3 to 6 carbon atoms, preferably the alkyl group is a methyl, and mixtures thereof;

in particular in the form of alkali metal or alkaline-earth metal, ammonium or amino alcohol salts.

The anionic surfactants comprising at least one sulfate function ($-OSO_3H$ or $-OSO_3^-$) may be chosen from the following compounds: alkylsulfates, alkylethersulfates, the alkylamidoethersulfates, alkylarylpolyethersulfates, monoglyceride-sulfates, and mixtures thereof; and the salts of these compounds; the alkyl groups of these compounds including from 6 to 30 carbon atoms, in particular from 6 to 20, better still from 8 to 16, even from 10 to 14 carbon atoms; the aryl group preferably denoting a phenyl or benzyl group; where these compounds may be polyoxyethylenated and then including preferably from 1 to 50 ethylene oxide units, better from 2 to 10 ethylene oxide units.

Preferably, the anionic surfactant comprising at least one sulfate function is chosen from:

alkylsulfates, the linear or branched alkyl group comprising from 6 to 24 carbon atoms, preferably from 6 to 20 carbon atoms, preferentially from 8 to 16 carbon atoms and better still from 10 to 14 carbon atoms;

alkylethersulfates, the linear or branched alkyl group comprising from 6 to 24 carbon atoms, preferably from 6 to 20 carbon atoms, preferentially from 8 to 16 carbon atoms and better still from 10 to 14 carbon atoms and preferably comprising from 2 to 20 ethylene oxide units, and mixtures thereof;

in particular in the form of alkali metal or alkaline-earth metal, ammonium or amino alcohol salts.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

In a preferred embodiment said anionic surfactant is chosen from (C6-C24)alkylsulfates, preferably (C6-C20) alkylsulfates, (C6-C24)alkylethersulfates, preferably (C6-C20)alkylethersulfates, (C6-C24)acylisethionates, preferably (C6-C20)acylisethionates, N—(C6-C24)acyl-N—(C1-C6)alkyltaurates, preferably N-acyl(C6-C20)—N-methyltaurates, and mixtures thereof; particularly in the form of alkali or alkaline earth metal, ammonium, or amino alcohol salts.

Preferably, said anionic surfactant is chosen from (C6-C24)alkylsulfates, preferably (C6-C20)alkylsulfates, (C6-C24)acylisethionates, preferably (C6-C20)acylisethionates, N—(C6-C24)acyl-N—(C1-C6)alkyltaurates, preferably N—(C6-C20)acyl-N-methyltaurates, and mixtures thereof; particularly in the form of alkali or alkaline earth metal, ammonium, or amino alcohol salts.

Better still, said anionic surfactant is chosen from (C6-C24)alkylsulfates, preferably (C6-C20)alkylsulfates, (C6-C24)acylisethionates, preferably (C6-C20)acylisethionates, and mixtures thereof; particularly in the form of alkali or alkaline earth metal, ammonium, or amino alcohol salts.

In a specific embodiment, said anionic surfactant is chosen from (C6-C24)acylisethionates, preferably (C6-C20) acylisethionates. Said anionic surfactant, when it is chosen from (C6-C24)acylisethionates, preferably (C6-C20)acylisethionates, produces compositions in particular exhibiting good cosmetic properties during application to keratin materials and to skin.

Examples of sulfonate surfactants that may be mentioned include alpha-olefin sulfonates, for instance sodium alpha-olefin sulfonate (C14-16), sold under the name Bio-Terge AS-40® by the company Stepan, sold under the names Witconate AOS Protege® and Sulframine AOS PH 12® by the company Witco or sold under the name Bio-Terge AS-40 CG® by the company Stepan, the secondary sodium olefin sulfonate sold under the name Hostapur SAS 30® by the company Clariant; linear alkylarylsulfonates such as sodium xylenesulfonate sold under the names Manrosol SXS30®, Manrosol SXS40® and Manrosol SXS93® by the company Manro.

Alkyl sulfoacetates that may be mentioned include lauryl sulfoacetate, for instance the product sold as a mixture with sodium methyl-2-sulfolaurate and disodium 2-sulfolaurate under the reference Stepan Mild PCL by the company Stepan. Mention may also be made of the sodium salt of lauryl sulfoacetate under the INCI name Sodium lauryl sulfoacetate and sold under the name Lathanol LAL® by the company Stepan.

Acylisethionates that may be mentioned include sodium cocoylisethionate, such as the product sold under the name Jordapon CI P® by the company Jordan, or the one sold under the name Hostapon SCI 85 P® by the company Clariant, and also sodium lauroyl methyl isethionate (for example Iselux LQ-CLR-SB from Innospec).

N-acyl-N-alkyltaurates that may be mentioned include the sodium salt of coconut oil methyltaurate sold under the name Hostapon CT Pate® by the company Clariant; sodium N-cocoy N-methyltaurate sold under the name Hostapon LT-SF® by the company Clariant or sold under the name Nikkol CMT-30-T® by the company Nikkol, and sodium palmitoyl methyltaurate sold under the name Nikkol PMT® by the company Nikkol.

Examples of alkyl ether sulfates that may be mentioned include sodium lauryl ether sulfate (CTFA name: sodium laureth sulfate), such as the product sold under the names Texapon® N40 and Texapon® N702 by the company Cognis, or ammonium lauryl ether sulfate (CTFA name: ammonium laureth sulfate), such as the product sold under the name Standapol® EA-2 by the company Cognis, or the ammonium (C12-C14)alkyl ether (9 EO) sulfate sold under the name Rhodapex AB/20® by the company Rhodia Chimie.

Alkyl sulfates that may be mentioned include for example sodium lauryl sulfate (CTFA name: sodium lauryl sulfate), such as the product sold by the company Tensachem under the name Tensopol USP94, or that sold under the name Texapon Z 95 P® by the company BASF, triethanolamine lauryl sulfate (CTFA name: TEA lauryl sulfate), such as the product sold by the company Huntsman under the name Empicol® TL40 FL or the product sold by the company Cognis under the name Texapon® T42, which products are at 40% in aqueous solution. Mention may also be made of ammonium lauryl sulfate (CTFA name: ammonium lauryl sulfate), such as the product sold by the company Huntsman under the name Empicol® AL 30FL, which is at 30% in aqueous solution.

The composition according to the invention may comprise from 0.2% to 2% by weight, and preferably from 0.4% to 1% by weight, of said anionic surfactants comprising at least one sulfate and/or sulfonate relative to the total weight of the composition.

Lipophilic Surfactants

The composition according to the invention comprises at least one lipophilic surfactant exhibiting an HLB less than or equal to 9. The lipophilic surfactant exhibiting an HLB less than or equal to 9 may be chosen from:
  a) (poly)glycerol esters comprising from 1 to 10 glycerol units and linear or branched, saturated or unsaturated C6-C24, preferably C8-C18 fatty acid(s):
    a. monoesters of glycerol and linear or branched, saturated or unsaturated C6-C24, preferably C8-C18 fatty acids, mention may for example be made of glyceryl oleate such as for example that sold by Cognis under the name of Monomuls 90-O 18; glyceryl stearate such as for example that sold by Cognis under the name of Cutina GMS V; glyceryl caprylate/caprate such as for example that sold by Stepan under the name of Stepan Mild GCC; glyceryl laurate such as for example that sold by Cognis under the name of Monomuls 90-L 12;
  b. polyglycerol monoesters comprising from 2 to 10 glycerol units and linear or branched, saturated or unsaturated C6-C24, preferably C8-C18, preferably C12-C18 fatty acids, mention may for example be made of polyglyceryl-3 ricinoleate (and) sorbitan isostearate such as for example that sold by Croda under the name of Arlacel 1690; polyglyceryl-4 isostearate such as for example that sold by Evonik Goldschmidt under the name of Isolan GI 34; polyglyceryl-3 ricinoleate such as for example that sold by Aarhuskarlshamn under the name of Akoline PGPR; the polyglyceryl-2 oleate such as for example that sold by Taiyo Kagaku under the name of Sunsoft Q-17B; polyglyceryl-2 caprylate such as for example that sold by Taiyo Kagaku under the name of Sunsoft Q-81B; polyglyceryl-2 laurate such as for example that sold by Taiyo Kagaku under the name of Sunsoft Q-12D;
  c. polyglycerol diesters comprising from 2 to 10 glycerol units and linear or branched, saturated or unsaturated C6-C24, preferably C8-C18 fatty acids, mention may in particular be made of polyglyceryl-2 distearate such as for example that sold by Nihon Emulsion under the name of Emalex PGSA;
  d. polyglycerol triesters comprising from 2 to 10 glycerol units and linear or branched, saturated or unsaturated C6-C24, preferably C8-C18 fatty acids, mention may be for example made of polyglyceryl-5 trioleate such as for example that sold by Taiyo Kagaku under the name of Sunsoft A-173E; polyglyceryl-5 trimyristate such as for example that sold by Taiyo Kagaku under the name of Sunsoft A-143E;
  e. polyglycerol pentaesters comprising from 2 to 10 glycerol units and linear or branched, saturated or unsaturated C6-C24, preferably C8-C18 fatty acids, mention may for example be made of polyglyceryl-10 pentaoleate such as for example that sold by Taiyo Kagaku under the name of Sunsoft Q-175S; polyglyceryl-10 pentastearate such as for example that sold by Taiyo Kagaku under the name of Sunsoft Q-185S;
  f. polyglycerol hexaesters comprising from 2 to 10 glycerol units and linear or branched, saturated or unsaturated C6-C24, preferably C8-C18 fatty acids: polyglyceryl-5 hexastearate such as for example that sold by Taiyo Kagaku under the name of Sunsoft A-186E;
  g. polyglycerol heptaesters comprising from 2 to 10 glycerol units and linear or branched, saturated or unsaturated C6-C24, preferably C8-C18 fatty acids, mention may for example be made of polyglyceryl-10 heptaoleate such as for example that sold by Taiyo Kagaku under the name of Sunsoft Q-177S;
  h. polyglycerol decaesters comprising from 2 to 10 glycerol units and linear or branched, saturated or unsaturated C6-C24, preferably C8-C18 fatty acids, mention may for example be made of polyglyceryl-10 decastearate such as for example that sold by Taiyo Kagaku under the name of Sunsoft Q-1810S;

i. polyglycerol polyesters comprising from 2 to 10 glycerol units and linear or branched, saturated or unsaturated C6-C24, preferably C8-C18 fatty acids, mention may for example be made of polyglyceryl-6 polyricinoleate such as for example that sold by Nikkol under the name of Hexaglyn PR-15; polyglyceryl-3 polyricinoleate such as for example that sold by Croda under the name of Crester PR;

b) polyglycerol esters comprising from 2 to 10 glycerol units and hydroxylated linear or branched, saturated or unsaturated C6-C24, preferably C12-C24 fatty polyacids such as polyglycerol diesters comprising from 2 to 10 glycerol units and hydroxylated fatty polyacids, particularly from 5 to 25 hydroxylated C12-C24 fatty acids, preferably from 6 to 15 C16-C20 hydroxylated fatty acids, mention may be made of polyglyceryl-2 dipolyhydroxystearate such as for example that sold by Cognis under the name of Dehymuls PGPH;

c) polyglycerol ethers comprising from 2 to 10 glycerol units and C6-C24, preferably C8-C18 fatty alcohols, mention may for example be made of polyglyceryl-2 oleyl ether such as for example that sold by Chimex under the name of Chimexane NB; polyglyceryl-4 oleyl ether such as for example that sold by Chimex under the name of Chimexane NC;

d) esters of sorbitol and/or sorbitan and linear or branched, preferably linear, saturated or unsaturated C6-C24, preferably C10-C22, preferably C12-C18, fatty acid(s) mention may in particular be made of sorbitan tristearate such as for example that sold by Croda under the name of Span 65; sorbitan sesquioleate such as for example that sold by Croda under the name of Arlacel 83 V; sorbitan isostearate such as for example that sold by Croda under the name of Arlacel 987; sorbitan oleate such as for example that sold by Croda under the name of Span 80 V; sorbitan stearate such as for example that sold by Cognis under the name of Dehymuls SMS; sorbitan laurate such as for example that sold by Cognis under the name of Dehymuls SML, sorbitan palmitate such as for example that sold by Croda under the name of Span 40;

e) esters of sucrose and C12-C18 fatty acids, mention may in particular be made of sucrose polystearate such as for example that sold by Sisterna under the name of Sisterna SP10-C; sucrose distearate such as for example that sold by Croda under the name of Crodesta F-10;

f) esters of methylglucose and linear or branched C12-C18 fatty acids such as for example methyl glucose isostearate such as for example that sold by Evonik Goldschmidt under the name of Isolan IS;

g) ethers of glucose and C12-C22 fatty alcohols, such as for example cetearyl glucoside (and) cetearyl alcohol such as for example that sold by Cognis under the name of Emulgade PL 68/50;

h) esters of glycol or polyethylene glycol and C12-C22, preferably C16-C18 fatty acids, such as glycol stearate such as for example that sold by Croda under the name EGMS N/E; PEG-2 stearate such as for example that sold by Croda under the name of Cithrol DEGMS N/E;

i) and mixtures thereof.

In a preferred embodiment, said lipophilic surfactant is chosen from polyglycerol esters comprising from 2 to 10 glycerol units and hydroxylated linear or branched, saturated or unsaturated C6-C24, preferably C12-C24, fatty polyacids. Also preferably, said lipophilic surfactant is chosen from polyglycerol diesters comprising from 2 to 10 glycerol units and hydroxylated fatty polyacids, particularly from 5 to 25 C12-C24 hydroxylated fatty acids, preferably from 6 to 15 hydroxylated C16-C20 fatty acids, and in particular polyglyceryl-2 dipolyhydroxystearate, such as for example that sold by the company Cognis (BASF) under the name of Dehymuls PGPH.

The composition according to the invention may comprise from 2% to 7% by weight and preferably from 3% to 5% by weight of lipophilic surfactants exhibiting an HLB less than or equal to 9, relative to the total weight of the composition.

In a preferred embodiment, said anionic surfactant is chosen from (C6-C24)alkylsulfates, (C6-C24)alkylethersulfates, N-acyl(C6-C24)-N—(C1-C6)alkyltaurates and (C6-C24)acylisethionates, and salts thereof and said lipophilic surfactant is chosen from polyglycerol diesters comprising from 2 to 10 glycerol units and hydroxylated fatty polyacids, particularly from 5 to 25 C6-C24 hydroxylated fatty acids.

According to a first specific embodiment, said anionic surfactant is chosen from (C6-C24)alkylsulfates and salts thereof and said lipophilic surfactant is chosen from polyglycerol esters comprising from 2 to 10 glycerol units and hydroxylated linear or branched, saturated or unsaturated C6-C24, preferably C12-C24 fatty polyacids. Preferably, said anionic surfactant is chosen from (C6-C20)alkylsulfates and salts thereof and said lipophilic surfactant is chosen from polyglycerol diesters comprising from 2 to 10 glycerol units and hydroxylated fatty polyacids, particularly from 5 to 25 hydroxylated C12-C24 fatty acids, better still, said anionic surfactant is sodium lauryl sulfate and said lipophilic surfactant is polyglyceryl-2 dipolyhydroxystearate.

According to a second specific embodiment, said anionic surfactant is chosen from (C6-C24)alkylethersulfates and salts thereof and said lipophilic surfactant is chosen from polyglycerol esters comprising from 2 to 10 glycerol units and hydroxylated linear or branched, saturated or unsaturated C6-C24, preferably C12-C24 fatty polyacids. Preferably, said anionic surfactant is chosen from (C6-C20)alkylethersulfates and salts thereof and said lipophilic surfactant is chosen from polyglycerol diesters comprising from 2 to 10 glycerol units and hydroxylated fatty polyacids, particularly from 5 to 25 hydroxylated C12-C24 fatty acids, better still, said anionic surfactant is sodium lauryl ether sulfate and said lipophilic surfactant is polyglyceryl-2 dipolyhydroxystearate.

According to a third specific embodiment, said anionic surfactant is chosen from N-acyl(C6-C24)-N—(C1-C6)alkyltaurates and salts thereof and said lipophilic surfactant is chosen from polyglycerol esters comprising from 2 to 10 glycerol units and hydroxylated linear or branched, saturated or unsaturated C6-C24, preferably C12-C24 fatty polyacids. Preferably, said anionic surfactant is chosen from the N-acyl(C6-C20)-N-methyltaurates and salts thereof and said lipophilic surfactant is chosen from polyglycerol diesters comprising from 2 to 10 glycerol units and hydroxylated fatty polyacids, particularly from 5 to 25 hydroxylated C12-C24 fatty acids, better still, said anionic surfactant is sodium cocoyl methyl taurate and said lipophilic surfactant is polyglyceryl-2 dipolyhydroxystearate.

According to a fourth specific embodiment, said anionic surfactant is chosen from (C6-C24)acylisethionates and salts thereof and said lipophilic surfactant is chosen from polyglycerol esters comprising from 2 to 10 glycerol units and hydroxylated linear or branched, saturated or unsaturated C6-C24, preferably C12-C24 fatty polyacids. Preferably, said anionic surfactant is chosen from (C6-C20)acylisethionates and salts thereof and said lipophilic surfactant is chosen from polyglycerol diesters comprising from 2 to 10 glycerol units and hydroxylated fatty polyacids, particularly from 5 to 25 hydroxylated C12-C24 fatty acids, better still, said anionic surfactant is sodium cocoyl isethionate and said lipophilic surfactant is polyglyceryl-2 dipolyhydroxystearate.

Said anionic surfactant and said lipophilic surfactant may be present in the composition according to the invention according to an anionic surfactant/lipophilic surfactant mass ratio "R" of between $1/10$ and $1/5$, preferably between $1/9$ and $1/8$.

Additional Surfactant(s)

The composition according to the invention comprises from 0% to 8% by weight of additional surfactant(s) by weight relative to the total weight of the composition.

"Additional surfactant(s)" is understood as any surfactant(s) distinct from the anionic surfactants comprising at least one sulfate and/or sulfonate function and the lipophilic surfactants exhibiting an HLB less than or equal to 9 as described previously.

The additional surfactant(s) may be chosen from anionic, cationic, amphoteric and non-ionic surfactants. The composition according to the invention is distinguished in particular from cleansing compositions by the low level of additional surfactant(s) and in particular the composition according to the invention comprises from 0% to 8% by weight of additional surfactant(s), preferably from 0% to 5% by weight of additional surfactant(s), preferably from 0% to 3% by weight of additional surfactant(s), better still from 0% to 1% by weight of additional surfactant(s) relative to the total weight of the composition. In particular, the composition according to the invention is devoid of additional surfactant.

Hydrophilic Thickener

The composition according to the present invention may also comprise at least one hydrophilic thickener, i.e. that is water-soluble or water-dispersible. This hydrophilic thickener may in particular have the effect of providing an increase in consistency of the emulsion.

Preferably, the hydrophilic thickener(s) are chosen from polysaccharides.

By way of polysaccharide, mention may in particular be made of scleroglucan gum, xanthan gum and derivatives thereof such as dehydroxanthan, guar gum, tara gum, ghatti gum, sclerotium gum, starches, agar, agarose, carrageenans, such as iota carrageenan, lambda carrageenan and kappa carrageenan, carob flour, alginates, celluloses and derivatives thereof, hydroxypropylguar, pectins and gellan gum.

Among the cellulose derivatives, mention may in particular be made of cellulose esters and/or alkyl ethers, such as ethylcelluloses, propylcelluloses, hydroxyethylcelluloses, hydroxypropylcelluloses or cellulose acetobutyrates.

In the context of the present invention, "sclerotium gum" and "scleroglucan" are equivalent terms, as is Sclerotium rolfsii gum. Indeed, the fungus Sclerotium rolfsii makes it possible to produce scleroglucan.

According to one embodiment, the composition relating to the present invention can contain mixtures of polysaccharides. Among these combinations, mention may in particular be made of:

scleroglucan gum and alginate,
xanthan gum and alginate, and
xanthan gum and guar gum.

The inventors have in fact noted that the consistency of the present composition can be improved by incorporating a first polysaccharide into the initial aqueous phase, preferably under hot conditions, for example at a temperature which may be between 60 and 80° C., then introducing a second polysaccharide at a lower temperature, which may, for example, range from 40 to 45° C., after the formation of the emulsion.

The hydrophilic thickener(s) can be comprised in the present composition in a content from 0.2% to 3% by weight, preferably from 0.4% to 2.5% by weight, or even from 0.5% to 2% by weight, relative to the total weight of the composition.

Pigments

In a specific embodiment, the composition according to the invention may comprise one or more pigments exhibiting an average size by volume greater than 100 nm.

For the purpose of the invention, the "size" of a particle means its D50. The D50, or volume average size, corresponds to the particle size defined such that 50% by volume of the particles have a size less than D50.

The volume average size may be assessed by light diffraction using a Malvern MasterSizer laser particle size analyser, said particles to be evaluated being in particular dispersed in a liquid medium, for instance octyldodecyl neopentanoate.

In this embodiment, the specific choice of anionic and lipophilic surfactants according to the invention produces compositions exhibiting good coverage, and a good soft focus effect.

"Soft-focus effect composition" is understood to mean a composition that can produce a blurred effect, making it possible to make the skin's microrelief optically matt and/or smooth, to fill wrinkles, hide skin imperfections and better reflect light.

The pigments having a particle size greater than 100 nm can be present in a proportion of from 0.1 to 40% by weight, preferably from 1 to 30% by weight, or even from 5 to 30% by weight, relative to the total weight of the composition containing them.

The term "pigments" should be understood as meaning white or coloured, mineral or organic particles that are insoluble in an aqueous solution, which are intended to colour and/or opacify the composition containing them.

The pigments may be white or coloured, and mineral and/or organic.

As mineral pigments of use in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

They may also be a pigment having a structure that may be, for example, of sericite/brown iron oxide/titanium dioxide/silica type. Such a pigment is sold, for example, under the reference Coverleaf NS or JS by the company Chemicals and Catalysts.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Mention may also be made of pigments treated and/or coated in a hydrophobic manner.

According to a specific embodiment of the invention, the pigments may be coated by at least one compound chosen from group constituted of silicone surface agents (such as organopolysiloxanes, silicone-acrylate copolymers, silicone resins, and mixtures thereof), fluorinated surface agents (such as polytetrafluoropolyethylene (PTFE)), fluorosilicone surface agents, metal soaps, particularly metal soaps of fatty acids having from 12 to 22 carbon atoms, N-acyl amino acids or salts thereof, particularly having from 8 to 22 carbon atoms, such as aluminium stearoyl glutamate, lecithin and its derivatives, isopropyl tristearoyl titanate, isostearyl sebacate, natural plant or animal waxes, polar synthetic waxes, fatty esters, phospholipids and mixtures thereof.

Advantageously, the pigments in accordance with the invention are iron oxides and/or titanium dioxides.

They can in particular be chosen from iron oxides (and) disodium stearoyl glutamate (and) aluminium hydroxide sold by the company Myoshi Kase under the name NAI-C33-7001-10, NAI-C33-8001-10 or NAI-C33-9001-10 or else titanium dioxide (and) disodium stearoyl glutamate (and) aluminium hydroxide sold by the company Myoshi Kase under the name NAI-TAO-77891.

Additionally, they may be chosen from titanium dioxides sold under the name Hombitan FF Pharma® by the company Sachtleben, iron oxides such as those sold under the names Sunpuro Red Iron Oxide C33-8001®, Sunpuro Yellow Iron Oxide C33-8001®, by the company Sun, or Unipure Triple Black LC 990 S by the company Sensient.

Provided that their presence does not affect the expected properties, the cosmetic composition of the present invention can also contain, in addition, pigments having an average size by volume of less than 100 nm.

Aqueous Phase

The composition according to the invention comprises an aqueous phase comprising water and/or hydrophilic solvents such as polyols.

The composition may comprise water at a concentration ranging from 0.5% to 95% by weight, preferably from 1% to 90% by weight, better from 10% to 80% by weight, and better still from 40% to 75% by weight, relative to the total weight of the composition.

The aqueous phase of the composition of the invention may comprise an organic solvent soluble in water, chosen for example from lower mono-alcohols including from 2 to 8 carbon atoms and particularly 2 to 6 carbon atoms, such as ethanol, isopropanol, propanol and butanol.

The aqueous phase may additionally comprise an organic solvent soluble in water at 25° C., chosen for example from polyols having in particular from 2 to 20 carbon atoms, preferably from 2 to 6 carbon atoms such as for example glycerine, propylene glycol, butylene glycol, hexylene glycol, dipropylene glycol, polyethylene glycols having from 2 to 200 ethylene oxide units, and mixtures thereof. Pentylene glycol, propanediol and mixtures thereof, are preferably used.

The amount of organic solvent soluble in water may range, for example, from 0.5 to 15% by weight, preferably from 0.5% to 10% by weight, better still from 1% to 10% by weight, even better still from 2% to 10% by weight and even better still from 2% to 8% by weight, relative to the total weight of the composition.

Fatty Phase

The fatty phase of the composition according to the invention comprises all the liposoluble or lipodispersible compounds present in the composition, including the fatty substances which are liquid at ambient temperature (25° C.) or oils (which form the oily phase), the fatty substances which are solid at ambient temperature, such as waxes, or else pasty compounds, fatty alcohols and fatty acids.

Thus, the composition according to the invention can comprise an oil which can be present in a content ranging from 0.5% to 40% by weight, preferably from 1% to 30% by weight and better still from 5% to 25% by weight, relative to the total weight of the composition.

As oils that may be used in the composition of the invention, mention may be made, for example, of:

hydrocarbon-based oils of animal origin, such as perhydrosqualene;

hydrocarbon-based oils of plant origin, such as liquid triglycerides of fatty acids including from 4 to 30 carbon atoms, for instance heptanoic or octanoic acid triglycerides, or alternatively, for example, jojoba oil, babassu oil, sunflower oil, olive oil, coconut oil, Brazil nut oil, manila oil, corn oil, soy bean oil, marrow oil, grapeseed oil, sesame seed oil, hazelnut oil, apricot oil, macadamia nut oil, arara oil, coriander oil, castor oil, avocado oil, caprylic/capric acid triglycerides, for instance those sold by the company Stéarinerie Dubois or those sold under the names Miglyol 810, 812 and 818 by the company Dynamit Nobel, and shea butter oil;

synthetic esters and ethers, in particular of fatty acids, for instance the oils having formulae $R^1COOR^2$ and $R^1OR^2$ in which $R^1$ represents a fatty acid residue or a fatty alcohol residue containing from 8 to 29 carbon atoms and $R^2$ represents a branched or unbranched hydrocarbon chain containing from 3 to 30 carbon atoms, for instance purcellin oil, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, isohexadecane, isododecane, and hydrogenated polyisobutene such as Parleam® oil;

silicone oils, for instance volatile or non-volatile polymethylsiloxanes (PDMS) containing a linear or cyclic silicone chain, which are liquid or pasty at ambient temperature, in particular volatile silicone oils, in particular cyclopolydimethylsiloxanes (cyclomethicones) such as cyclohexadimethylsiloxane and cyclopentadimethylsiloxane; polydimethylsiloxanes including alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyltrimethylsiloxysilicates and polymethylphenylsiloxanes;

mixtures thereof.

Mention may also be made of the following oils:

esters derived from the reaction of at least one fatty acid comprising at least 6 carbon atoms, preferably from 6 to 26 carbon atoms, better still from 6 to 20 carbon atoms and even better still from 6 to 16 carbon atoms and of at least one alcohol comprising from 1 to 17 carbon atoms and better still from 3 to 15 carbon atoms; mention may be made in particular of isopropyl myristate, isopropyl palmitate, 2-ethylhexyl caprate/caprylate (or octyl caprate/caprylate), 2-ethylhexyl palmitate, isostearyl neopentanoate, isononyl isononanoate, hexyl laurate, esters of lactic acid and fatty alcohols comprising 12 or 13 carbon atoms, diesters of carbonic acid and fatty alcohols comprising from 6 to 10 carbon atoms such as dicaprylyl carbonate such as that sold under the name by Cetiol CC by the company Cognis, fatty alcohol ethers comprising from 6 to 20 carbon atoms, such as dicaprylyl ether (Cetiol OE from Cognis), glycerol ethers comprising from 6 to 12 carbon atoms, for instance the 2-ethylhexyl ether of glycerol (INCI name: ethylhexyl glycerol) such as Sensiva SC 50 from the company Schulke & Mayr GmbH.

Preferably, the oil phase of the composition comprises an oil chosen from hydrocarbon oils of plant origin, linear or branched hydrocarbons, or ester oils.

The cosmetic compositions of the invention may also contain adjuvants that are common in the cosmetics field, such as antioxidants, preservatives, fragrances, fragrance peptizers, colorants, fillers, or hydrophilic or lipophilic active agents. The nature of the adjuvants and the amounts thereof should be such that they do not modify the properties of the composition according to the invention. The amounts of these adjuvants are those conventionally used in the cosmetics field, for example from 0.001% to 10% of the total weight of the composition.

Needless to say, a person skilled in the art will take care to select the optional additive(s) to be added to the composition according to the invention such that the advantageous properties intrinsically associated with the composition in accordance with the invention are not, or are not substantially, adversely affected by the envisaged addition.

The composition according to the invention may moreover comprise one or more fillers. Fillers that may be mentioned include mineral fillers such as talc or magnesium silicate (particle size: 5 microns) sold under the name Luzenac 15 M00® by the company Luzenac, kaolin or aluminium silicate, for instance the product sold under the name Kaolin Supreme® by the company Imerys, or organic fillers such as starch, for instance the product sold under the name Amidon de Mals B® by the company Roquette, polyamide (Nylon) microspheres such as those sold under the name Orgaso12002 UD Nat Cos® by the company Arkema, microspheres based on expanded vinylidene chloride/acrylonitrile/methacrylonitrile copolymer containing isobutane, such as the products sold under the name Expancel 551 DE® by the company Expancel. Fillers may be present in the composition according to the invention at between 0.01% and 40% by weight, preferably between 0.05% and 15% by weight and better still between 0.1% and 5% by weight relative to the total weight of the composition.

The compositions according to the invention are intended to be applied to keratin materials such as the skin (body, face, eyes, scalp).

The composition according to the invention may also comprise one or more pearlizers. The term "pearlizers" should be understood as meaning iridescent or non-iridescent coloured particles of any shape, in particular produced by certain molluscs in their shell or alternatively synthesized, which exhibit a colour effect via optical interference.

In a preferred embodiment, the pearlizers may be present in the composition according to the invention at between 0.01% and 40% by weight, preferably between 0.05% and 15% by weight and better still between 0.1% and 5% by weight relative to the total weight of the composition.

The pearlizers may be chosen from pearlizing pigments such as titanium mica coated with an iron oxide, titanium mica coated with bismuth oxychloride, titanium mica coated with chromium oxide, titanium mica coated with an organic dye and also pearlizing pigments containing bismuth oxychloride. They may also be mica particles, at the surface of which are superposed at least two successive layers of metal oxides and/or of organic dyestuffs.

Examples of pearlizers that may also be mentioned include natural mica coated with titanium oxide, with iron oxide, with natural pigment or with bismuth oxychloride.

Among the pearlizers available on the market, mention may be made of the pearlizers Timica, Flamenco and Duochrome (based on mica) sold by the company Engelhard, the Timiron pearlizers sold by the company Merck, the Prestige mica-based pearlizers sold by the company Eckart, and the Sunshine synthetic mica-based pearlizers sold by the company Sun Chemical.

The pearlizers may more particularly have a yellow, pink, red, bronze, orangey, brown, gold and/or coppery colour or sparkle.

As illustrations of pearlizers that may be used in the context of the present invention, mention may be made of gold-coloured pearlizers sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze pearlizers sold in particular by the company Merck under the names Bronze fine (17384) (Colorona) and Bronze (17353) (Colorona) and by the company Engelhard under the name Super bronze (Cloisonne); the orange pearlizers sold in particular by the company Engelhard under the names Orange 363C (Cloisonne) and Orange MCR 101 (Cosmica) and by the company Merck under the names Passion orange (Colorona) and Matte orange (17449) (Microna); the brown-tinted pearlizers sold in particular by the company Engelhard under the names Nu-antique copper 340XB (Cloisonne) and Brown CL4509 (Chromalite); the pearlizers with a copper tint sold in particular by the company Engelhard under the name Copper 340A (Timica); the pearlizers with a red tint sold in particular by the company Merck under the name Sienna fine (17386) (Colorona); the pearlizers with a yellow tint sold in particular by the company Engelhard under the name Yellow (4502) (Chromalite); the red-tinted pearlizers with a golden tint sold in particular by the company Engelhard under the name Sunstone G012 (Gemtone); the pink pearlizers sold in particular by the company Engelhard under the name Tan opal G005 (Gemtone); the black pearlizers with a golden tint sold in particular by the company Engelhard under the name Nu antique bronze 240 AB (Timica); the blue pearlizers sold in particular by the company Merck under the name Matte blue (17433) (Microna); the white pearlizers with a silvery tint sold in particular by the company Merck under the name Xirona Silver; and the golden-green pinkish-orange pearlizers sold in particular by the company Merck under the name Indian summer (Xirona), and mixtures thereof.

Advantageously, the pearlizers in accordance with the invention are micas coated with titanium dioxide or with iron oxide, and also bismuth oxychloride.

The composition according to the present invention may also comprise particles with a metallic sparkle. For the purposes of the present invention, the term "particles with a metallic sparkle" means any compound whose nature, size, structure and surface finish allow it to reflect incident light, in particular in a non-iridescent manner.

A composition according to the invention may comprise from 0.1% to 50% by weight and preferably from 1% to 20% by weight of particles with a metallic sparkle relative to the total weight of said composition.

Particles with a substantially flat outer surface are also suitable, since they can, if their size, structure and surface finish allow it, more easily give rise to a strong specular reflection, which may then be termed a mirror effect.

Particles with a metallic sparkle that may be used in the invention may, for example, reflect light in all the components of the visible region without significantly absorbing one or more wavelengths. The spectral reflectance of these particles may, for example, be greater than 70% and better still at least 80%, or even 90% or 95%, in the range 400-700 nm.

These particles generally have a thickness of less than or equal to 1 µm, in particular less than or equal to 0.7 µm and in particular less than or equal to 0.5 µm.

Particles with a metallic sparkle that may be used in the invention are in particular chosen from:

particles of at least one metal and/or of at least one metal derivative;

particles comprising a monomaterial or multimaterial organic or inorganic substrate, at least partially coated with at least one layer with a metallic sparkle comprising at least one metal and/or at least one metal derivative; and mixtures of said particles.

Among the metals that may be present in said particles, mention may for example be made of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr, and mixtures or alloys thereof (for example bronzes and brasses) are preferred metals.

The term "metal derivatives" denotes compounds derived from metals, in particular oxides, fluorides, chlorides and sulfides.

Among the metal derivatives that may be present in said particles, mention may be made in particular of metal oxides, for instance titanium oxide, in particular $TiO_2$, iron oxide, in particular $Fe_2O_3$, tin oxide, chromium oxide, barium sulfate and the following compounds: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$, and mixtures or alloys thereof.

Illustrations of these particles that may be mentioned include aluminium particles, such as those sold under the names Starbrite 1200 EAC® by the company Silberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

As illustrations of particles of this second type, mention may be made more particularly of:

Glass particles coated with a metallic layer, in particular those described in documents JP-A-09188830, JP-A-10158450, JP-A-10158541, JP-A-07258460 and JP-A-05017710.

As illustration of these particles including a glass substrate, mention may be made of those coated respectively with silver, gold or titanium, in the shape of platelets, sold by the company Nippon Sheet Glass under the name Microglass Metashine. Particles comprising a glass substrate coated with silver, in the form of platelets, are sold under the name Microglass Metashine REFSX 2025 PS by Toyal. Particles with a glass substrate coated with nickel/chromium/molybdenum alloy are sold under the name Crystal Star GF 550 and GF 2525 by this same company. Those coated either with brown iron oxide or with titanium oxide, tin oxide or a mixture thereof, for instance those sold under the name Reflecks by the company Engelhard or those sold under the name Metashine MC 2080GP by the company Nippon Sheet Glass.

These metal-coated glass particles may be coated with silica, for instance those sold under the name Metashine series PSS1 or GPS1 by the company Nippon Sheet Glass.

Particles with spherical glass substrates coated or not coated by a metal, in particular those sold under the name Prizmalite Microsphere by the company Prizmalite Industries.

Pigments of the Metashine 1080R range sold by the company Nippon Sheet Glass Co. Ltd are also suitable for the invention. These pigments, more particularly described in patent application JP 2001-11340, are C-Glass glass flakes comprising 65% to 72% $SiO_2$, coated with a layer of rutile titanium oxide ($TiO_2$). These glass flakes have a mean thickness of 1 micron and a mean size of 80 microns, i.e. a mean size/mean thickness ratio of 80. They have blue, green or yellow sparkles or a silver shade depending on the thickness of the $TiO_2$ layer.

Particles including a silver-coated borosilicate substrate, also known as "white pearlizers".

Particles comprising a metal substrate such as aluminium, copper or bronze, in the form of platelets, are sold under the trade name Starbrite by the company Silberline and under the name Visionaire by the company Eckart.

Particles comprising a synthetic mica substrate coated with titanium dioxide, and for example particles with a size of between 80 and 100 µm, comprising a synthetic mica (fluorophlogopite) substrate coated with titanium dioxide representing 12% of the total weight of the particle, sold under the name Prominence by the company Nihon Koken.

The particles with a metallic sparkle may also be chosen from particles formed from a stack of at least two layers with different refractive indices. These layers may be of polymeric or metallic nature and may in particular include at least one polymer layer.

Thus, the particles with a metallic effect may be particles derived from a multilayer polymer film.

The choice of materials intended to constitute the various layers of the multilayer structure is obviously made so as to give the particles thus formed the desired metallic effect. Such particles are in particular described in WO 99/36477, U.S. Pat. Nos. 6,299,979 and 6,387,498 and more particularly identified below in the goniochromatic section.

Advantageously, the particles with a metallic sparkle in accordance with the invention are particles with a spherical or non-spherical glass substrate, and also particles with a metallic substrate.

Some of these materials may also be used in a composite form. Composite pigments that may in particular be mentioned in this respect include those described in patent EP 1 184 426. These composite pigments may in particular be composed of particles comprising a mineral core at least partially coated with an organic pigment and at least one binder for fixing the organic pigments to the core.

The examples that follow are given as illustrations of the invention and are not limiting in nature. All the amounts are given as weight percentages relative to the total weight of the composition. The names of the compounds are indicated, depending on the case, as the chemical names or the INCI names.

EXAMPLES

1. Compositions Without Pigments

Compositions 1 to 6 as described below were made. Compositions 1 to 4 correspond to compositions according to the invention whereas compositions 5 and 6 correspond to compositions outside the invention. Compositions 5 and 6 outside the invention are distinguished from the compositions according to the invention in that they do not comprise the anionic surfactants as previously cited. For each of compositions 1 to 6 the duration of application or "playtime" was evaluated on the skin. For each of compositions 1 to 5 the stability was evaluated at 55° C. for 15 days.

| INCI name | Composition No. 1 according to the invention | Composition No. 2 according to the invention | Composition No. 3 according to the invention | Composition No. 4 according to the invention |
|---|---|---|---|---|
| SODIUM HYDROXIDE | qs pH = 5 | qs pH = 5 | qs pH = 5 | qs pH = 5 |
| BENZYL ALCOHOL | 0.5 | 0.5 | 0.5 | 0.5 |
| JOJOBA OIL | 5 | 5 | 5 | 5 |
| DICAPRYLYL ETHER | 9 | 9 | 9 | 9 |
| FRAGRANCE | 0.1 | 0.1 | 0.1 | 0.1 |
| XANTHAN GUM | 0.4 | 0.4 | 0.4 | 0.4 |
| SCLEROGLUCAN GUM | 0.4 | 0.4 | 0.4 | 0.4 |
| SODIUM ALGINATE | 0.1 | 0.1 | 0.1 | 0.1 |
| ETHYL ALCOHOL | 3 | 3 | 3 | 3 |
| WATER | 65.03 qs | 64 qs | 64.84 qs | 64.97 qs |
| GLYCERINE | 7 | 7 | 7 | 7 |
| UNDECANE AND TRIDECANE | 5 | 5 | 5 | 5 |
| SODIUM METHYL COCOYL TAURATE IN AQUEOUS DISPERSION AT 30% (1) | — | 1.5 (=0.45 AI) | — | — |
| SODIUM LAURETH SULFATE IN AQUEOUS SOLUTION AT 70% (2) | — | — | 0.66 (=0.46 AI) | — |
| SODIUM LAURYL SULFATE( 3) | 0.47 | — | — | — |
| POLYGLYCERYL-2 DIPOLYHYDROXYSTEARATE (4) | 4 | 4 | 4 | 4 |
| SODIUM COCOYL ISETHIONATE (5) | — | — | — | 0.53 (=0.47 AI) |
| Anionic surfactant/lipophilic surfactant mass ratio | 1/9 | 1/9 | 1/9 | 1/9 |

*AI: active ingredient (1) SODIUM COCOYL METHYL TAURATE IN AQUEOUS DISPERSION AT 30% BY WEIGHT OF ACTIVE INGREDIENT SOLD UNDER THE NAME HOSTAPON CT PATE ® BY CLARIANT;

(2) SODIUM LAURETH SULFATE IN AQUEOUS SOLUTION AT 70% BY WEIGHT OF ACTIVE INGREDIENT SOLD UNDER THE NAME TEXAPON N702 ® BY BASF;

(3) SODIUM LAURYL SULFATE SOLD UNDER THE NAME TEXAPON Z 95 P ® BY BASF;

(4) POLYGLYCERYL-2 DIPOLYHYDROXYSTEARATE SOLD UNDER THE NAME DEHYMULS PGPH ® BY COGNIS;

(5) SODIUM COCOYL ISETHIONATE AT 88% BY WEIGHT OF ACTIVE INGREDIENT SOLD UNDER THE NAME HOSTAPON SCI 85 P ® BY CLARIANT.

| INCI name | Composition No. 5 outside the invention | Composition No. 6 outside the invention |
|---|---|---|
| SODIUM HYDROXIDE | qs pH = 5 | qs pH = 5 |
| BENZYL ALCOHOL | 0.5 | 0.5 |
| JOJOBA OIL | 5 | 5 |
| DICAPRYLYL ETHER | 9 | 9 |
| FRAGRANCE | 0.1 | 0.1 |
| XANTHAN GUM | 0.4 | 0.4 |
| SCLEROGLUCAN GUM | 0.4 | 0.4 |
| SODIUM ALGINATE | 0.1 | 0.1 |
| ETHYL ALCOHOL | 3 | 3 |
| WATER | 64 qs | 65.03 qs |
| GLYCERINE | 7 | 7 |
| UNDECANE AND TRIDECANE | 5 | 5 |
| POLYGLYCERYL-2 DIPOLYHYDROXYSTEARATE (4) | 4 | 4 |
| SODIUM LAURYL GLUCOSE CARBOXYLATE (AND) LAURYL GLUCOSIDE (6) | 1.5 (=0.45 AI) | — |
| DISODIUM CETEARYL SULFOSUCCINATE (7) | — | 0.47 AI |
| Anionic surfactant/lipophilic surfactant mass ratio | 1/9 | 1/9 |

*AI: active ingredient
(6) SODIUM LAURYL GLUCOSE CARBOXYLATE (and) LAURYL GLUCOSIDE AT 30% BY WEIGHT OF ACTIVE INGREDIENT SOLD UNDER THE NAME PLANTAPON LGC SORB ® BY COGNIS
(7) DISODIUM CETEARYL SULFOSUCCINATE SOLD UNDER THE NAME EUMULGIN PRISMA ® BY BASF Manufacturing Process for Compositions 1 to 6
  a. Using a saw-tooth blade, form the gel (xanthan gum+ sodium alginate) at 80° C. in water containing glycerine and the preservative. Then add the hydrophilic surfactant just before emulsification at 55° C.
  b. During this period, heat the oil phase (containing jojoba oil, dicaprylyl ether and the mixture of undecane and tridecane) in the water bath at 55° C.
  c. At 55° C., with a rotor-stator, emulsify the oil phase on the aqueous phase. Stir vigorously for 5 minutes, then add the scleroglucan gum in a fine rain.
  d. Cool the emulsion formed to ambient temperature with gentle stirring.
  e. Add the ethanol and fragrance at ambient temperature then adjust the pH to 4.8.

1.1 Evaluation of the Stability of Compositions 1 to 5.

Each of compositions 1 to 5 was stored at a temperature of 55° C. for a duration of 15 days. The macroscopic appearance was evaluated. The results obtained are presented in the table below after a duration of 15 days.

| Evaluated criterion | Composition No. 1 according to the invention | Composition No. 2 according to the invention | Composition No. 3 according to the invention | Composition No. 4 according to the invention |
|---|---|---|---|---|
| Macroscopic appearance (to the naked eye) | homogeneous, smooth, pliant, non-fluid cream | homogeneous, smooth, pliant, non-fluid cream | homogeneous, smooth, pliant, non-fluid cream | homogeneous, smooth, pliant, non-fluid cream |

| Criteria evaluated | Composition No. 5 outside the invention |
|---|---|
| Macroscopic appearance (to the naked eye) | The colour changes from white to off-white and a transparent border at the surface |

The results obtained show that compositions 1 to 4 according to the invention exhibit a macroscopic appearance that does not change over time (15 days) at a temperature of 55° C. by contrast with compositions 5 and 6 outside the invention. Accordingly, compositions 1 to 4 remain stable over time.

1.2 Evaluation of the Duration of Application or Playtime of Compositions 1 to 6 on Skin The playtime is measured by applying 50 μL of each of compositions 1 to 6 to a porous hydrophobic Durapore membrane filter GVHP® 0.22 μm by the company EMD-Millipore exhibiting a diameter of 4.7 cm.

The specific choice of this filter, which is hydrophobic and porous provides a support similar to that of skin and relevant to evaluate the criterion of playtime.

The composition is spread on the filter with two fingers in a circular manner at a frequency of 1 circle per second. The result obtained corresponds to the duration (in seconds) necessary to produce total product penetration in the filter, also corresponding to the number of circles to produce total penetration of the product in the filter.

The results obtained are shown in the table below.

| Evaluated criterion | Composition No. 1 according to the invention | Composition No. 2 according to the invention | Composition No. 3 according to the invention | Composition No. 4 according to the invention |
|---|---|---|---|---|
| Duration of application or "playtime" in seconds | 68.8 | 55.4 | 69.6 | 61.2 |

| Evaluated criterion | Composition No. 5 outside the invention | Composition No. 6 outside the invention |
|---|---|---|
| Duration of application or "playtime" in seconds | 44.2 | 41.2 |

The results above show that compositions 1 to 4 according to the invention have a longer duration of application on skin than those of compositions 5 and 6 outside the invention. Accordingly, the specific combination of surfactants according to the invention produces a satisfactory "playtime".

2. Compositions Comprising Pigments

Compositions 7 to 11 as described below were made.

Compositions 7 to 10 correspond to compositions according to the invention whereas composition 11 corresponds to compositions outside the invention.

For each of compositions 7 to 11 the stability was evaluated at ambient temperature (25° C.) for 2 months.

| INCI name | Composition No. 7 according to the invention | Composition No. 8 according to the invention | Composition No. 9 according to the invention | Composition No. 10 according to the invention |
|---|---|---|---|---|
| SODIUM HYDROXIDE | qs pH = 5 | qs pH = 5 | qs pH = 5 | qs pH = 5 |
| TITANIUM DIOXIDE AND DISODIUM STEAROYL GLUTAMATE AND ALUMINIUM HYDROXIDE (8) | 10.998 | 10.998 | 10.998 | 10.998 |
| RED IRON OXIDE AND ALUMINIUM STEAROYL GLUTAMATE AND ALUMINIUM HYDROXIDE (9) | 0.477 | 0.477 | 0.477 | 0.477 |
| BLACK IRON OXIDE AND DISODIUM STEAROYL GLUTAMATE AND ALUMINIUM HYDROXIDE (10) | 0.198 | 0.198 | 0.198 | 0.198 |
| YELLOW IRON OXIDE AND DISODIUM STEAROYL GLUTAMATE AND ALUMINIUM HYDROXIDE (11) | 2.322 | 2.322 | 2.322 | 2.322 |
| MICA (SYNTHETIC FLUOROPHLOGOPITE) (10-50 µM) (12) | 1.555 | 1.555 | 1.555 | 1.555 |
| BENZYL ALCOHOL | 0.5 | 0.5 | 0.5 | 0.5 |
| JOJOBA OIL | 5 | 5 | 5 | 5 |
| DICAPRYLYL ETHER | 9 | 9 | 9 | 9 |
| FRAGRANCE | 0.1 | 0.1 | 0.1 | 0.1 |
| XANTHAN GUM | 0.4 | 0.4 | 0.4 | 0.4 |
| SCLEROGLUCAN GUM | 0.4 | 0.4 | 0.4 | 0.4 |
| SODIUM ALGINATE | 0.1 | 0.1 | 0.1 | 0.1 |
| ETHYL ALCOHOL | 3 | 3 | 3 | 3 |
| WATER | 49.48 qs | 48.45 qs | 49.29 qs | 49.42 qs |
| GLYCERINE | 7 | 7 | 7 | 7 |
| UNDECANE AND TRIDECANE | 5 | 5 | 5 | 5 |
| SODIUM METHYL COCOYL TAURATE IN AQUEOUS DISPERSION AT 30% (1) | — | 1.5 (=0.45 AI) | — | — |
| SODIUM LAURETH SULFATE IN AQUEOUS SOLUTION AT 70% (2) | — | — | 0.66 (=0.46 AI) | — |
| SODIUM LAURYL SULFATE (3) | 0.47 | — | — | — |
| POLYGLYCERYL-2 DIPOLYHYDROXYSTEARATE (4) | 4 | 4 | 4 | 4 |
| SODIUM COCOYL ISETHIONATE (5) | — | — | — | 0.53 (=0.47 AI) |
| Anionic surfactant/lipophilic surfactant mass ratio | 1/9 | 1/9 | 1/9 | 1/9 |

(1) SODIUM COCOYL METHYL TAURATE IN AQUEOUS DISPERSION AT 30% BY WEIGHT OF ACTIVE INGREDIENT SOLD UNDER THE NAME HOSTAPON CT PATE ® BY CLARIANT;
(2) SODIUM LAURETH SULFATE IN AQUEOUS SOLUTION AT 70% BY WEIGHT OF ACTIVE INGREDIENT SOLD UNDER THE NAME TEXAPON N702 ® BY BASF;
(3) SODIUM LAURYL SULFATE SOLD UNDER THE NAME TEXAPON Z 95 P ® BY BASF;
(4) POLYGLYCERYL-2 DIPOLYHYDROXYSTEARATE SOLD UNDER THE NAME DEHYMULS PGPH ® BY COGNIS;
(5) SODIUM COCOYL ISETHIONATE AT 88% BY WEIGHT OF ACTIVE INGREDIENT SOLD UNDER THE NAME HOSTAPON SCI 85 P ® BY CLARIANT;
(8) TITANIUM DIOXIDE AND DISODIUM STEAROYL GLUTAMATE AND ALUMINIUM HYDROXIDE SOLD UNDER THE NAME NAI-TAO-77891 BY MIYOSHI KASEI;
(9) RED IRON OXIDE AND ALUMINIUM STEAROYL GLUTAMATE AND ALUMINIUM HYDROXIDE SOLD UNDER THE NAME NAI-C33-8001-10 BY MIYOSHI KASEI;
(10) BLACK IRON OXIDE AND DISODIUM STEAROYL GLUTAMATE AND ALUMINIUM HYDROXIDE SOLD UNDER THE NAME NAI-C33-7001-10 BY MIYOSHI KASEI;
(11) YELLOW IRON OXIDE AND DISODIUM STEAROYL GLUTAMATE AND ALUMINIUM HYDROXIDE SOLD UNDER THE NAME NAI-C33-9001-10 BY MIYOSHI KASEI;
(12) MICA (SYNTHETIC FLUOROPHLOGOPITE) (10-50 µM) SOLD UNDER THE NAME SYNAFIL S 1050 BY ECKART.

| INCI name | Composition No. 11 outside the invention |
|---|---|
| SODIUM HYDROXIDE | qs pH = 5 |
| TITANIUM DIOXIDE AND DISODIUM STEAROYL GLUTAMATE AND ALUMINIUM HYDROXIDE (8) | 10.998 |
| RED IRON OXIDE AND ALUMINIUM STEAROYL GLUTAMATE AND ALUMINIUM HYDROXIDE (9) | 0.477 |
| BLACK IRON OXIDE AND DISODIUM STEAROYL GLUTAMATE AND ALUMINIUM HYDROXIDE (10) | 0.198 |
| YELLOW IRON OXIDE AND DISODIUM STEAROYL GLUTAMATE AND ALUMINIUM HYDROXIDE (11) | 2.322 |
| MICA (SYNTHETIC FLUOROPHLOGOPITE) (10-50 μM) (12) | 1.555 |
| BENZYL ALCOHOL | 0.5 |
| JOJOBA OIL | 5 |
| DICAPRYLYL ETHER | 9 |
| FRAGRANCE | 0.1 |
| XANTHAN GUM | 0.4 |
| SCLEROGLUCAN GUM | 0.4 |
| SODIUM ALGINATE | 0.1 |
| ETHYL ALCOHOL | 3 |
| WATER | 48.45 qs |
| GLYCERINE | 7 |
| UNDECANE AND TRIDECANE | 5 |
| POLYGLYCERYL-2 DIPOLYHYDROXYSTEARATE (4) | 4 |
| SODIUM LAURYL GLUCOSE CARBOXYLATE (AND) LAURYL GLUCOSIDE (6) | 1.5 (=0.45 AI) |
| Anionic surfactant/lipophilic surfactant mass ratio | 1/9 |

(6) SODIUM LAURYL GLUCOSE CARBOXYLATE AND LAURYL GLUCOSIDE AT 30% BY WEIGHT OF ACTIVE INGREDIENT SOLD UNDER THE NAME PLANTAPON LGC SORB BY COGNIS;
(8) TITANIUM DIOXIDE AND DISODIUM STEAROYL GLUTAMATE AND ALUMINIUM HYDROXIDE SOLD UNDER THE NAME NAI-TAO-77891 BY MIYOSHI KASEI;
(9) RED IRON OXIDE AND ALUMINIUM STEAROYL GLUTAMATE AND ALUMINIUM HYDROXIDE SOLD UNDER THE NAME NAI-C33-8001-10 BY MIYOSHI KASEI;
(10) BLACK IRON OXIDE AND DISODIUM STEAROYL GLUTAMATE AND ALUMINIUM HYDROXIDE SOLD UNDER THE NAME NAI-C33-7001-10 BY MIYOSHI KASEI;
(11) YELLOW IRON OXIDE AND DISODIUM STEAROYL GLUTAMATE AND ALUMINIUM HYDROXIDE SOLD UNDER THE NAME NAI-C33-9001-10 BY MIYOSHI KASEI;
(12) MICA (SYNTHETIC FLUOROPHLOGOPITE) (10-50 μM) SOLD UNDER THE NAME SYNAFIL S 1050 BY ECKART.

Preparation Process for Compositions 7 to 11.

a. Using a saw-tooth blade, form the gel (xanthan gum+ sodium alginate) at 80° C. in water containing glycerine and the preservative. Then add the hydrophilic surfactant just before emulsification at 55° C.

b. During this period, heat the oil phase (containing jojoba oil, dicaprylyl ether and the mixture of undecane and tridecane) in the water bath at 55° C. When the mixture has reached 55° C., add the titanium oxide, iron oxides and mica using the saw-tooth blade.

c. At 55° C., with a rotor-stator, emulsify the oil phase on the aqueous phase. Stir vigorously for 5 minutes, then add the scleroglucan gum in a fine rain.

d. Cool to the emulsion formed to ambient temperature with gentle stirring.

e. Add the ethanol and fragrance at ambient temperature then adjust the pH to 4.8.

2.1 Evaluation of the Stability of Compositions 7 to 11.

Each of compositions 7 to 11 was stored at ambient temperature (25° C.) for a duration of 2 months. The macroscopic appearance and viscosity were evaluated. The results obtained are shown in the table below.

| Criteria evaluated | Composition No. 7 according to the invention | Composition No. 8 according to the invention | Composition No. 9 according to the invention | Composition No. 10 according to the invention |
|---|---|---|---|---|
| Viscosity (in poises) at T 24 h at ambient temperature | 17 | 17.8 | 15.3 | 16.6 |
| Viscosity (in poises) at T 2 months at ambient temperature | 16.6 | 17 | 17 | 16.1 |
| Macroscopic appearance (to the naked eye) | homogeneous, smooth, pliant, non-fluid cream | homogeneous, smooth, pliant, non-fluid cream | homogeneous, smooth, pliant, non-fluid cream | homogeneous, smooth, pliant, non-fluid cream |

| Criteria evaluated | Composition No. 11 outside the invention |
|---|---|
| Viscosity (in poises) at T 24 h at ambient temperature | 19.9 |
| Viscosity (in poises) at T 2 months at ambient temperature | 9 |
| Macroscopic appearance (to the naked eye) | brown mottling on the surface, less smooth, granular formula |

The results above show that the viscosity of compositions No. 7 to 10 according to the invention remain constant whereas composition 11 outside the invention shows a viscosity drop of 10.9 poises, i.e. a viscosity drop of more than 50% relative to the initial value measured at T 24 h. Accordingly, the compositions according to the invention 7 to 10 remain stable for two months at ambient temperature by contrast with composition 11. Also, we observe that composition No. 11 outside the invention exhibits, after two months at ambient temperature, brown mottling on the surface, and a less smooth, granular appearance, by contrast with compositions No. 7 to 10 according to the invention whose macroscopic appearance does not change after 2 months at ambient temperature.

The invention claimed is:

1. A cosmetic composition having the form of an oil-in-water emulsion comprising:
   i) at least one lipophilic surfactant with HLB less than or equal to 9,
   (ii) at least one anionic surfactant comprising at least one group selected from the group consisting of (C6-C30) alkylsulfonates, (C6-C30)alkylamidesulfonates, (C6-C30)alkylarylsulfonates, alpha-olefin-sulfonates, paraffin-sulfonates, (C6-C30)alkylsulfoacetates, N-acyl (C6-C30)-N—(C1-C6)alkyltaurates, (C6-C30) acylisethionates, (C6-C30)alkylsulfolaurates, and salts thereof, and mixtures thereof;
   said composition comprising from 0% to 8% by weight of additional surfactant(s) relative to the total weight of the composition,
   wherein the cosmetic composition is phase inverted upon application, and
   wherein the additional surfactant(s), if present, do not comprise at least one nonionic surfactant.

2. The cosmetic composition according to claim 1, wherein said lipophilic surfactant is selected from the group consisting of (poly)glycerol esters comprising from 1 to 10 glycerol units and linear or branched, saturated or unsaturated C6-C24, fatty acid(s), polyglycerol esters comprising from 2 to 10 glycerol units and hydroxylated linear or branched, saturated or unsaturated C6-C24, fatty polyacids, polyglycerol ethers comprising from 2 to 10 glycerol units and C6-C24, esters of sorbitol and/or sorbitan and linear or branched, saturated or unsaturated C6-C24 fatty acid(s), esters of sucrose and C12-C18 fatty acid(s), esters of methylglucose and linear or branched C12-C18 fatty acid, ethers of glucose and C12-C22 fatty alcohol, esters of glycol or polyethylene glycol and a C12-C22 fatty acid, and mixtures thereof.

3. The cosmetic composition according to claim 1, wherein said lipophilic surfactant is selected from the group consisting of polyglycerol diesters comprising from 2 to 10 glycerol units and hydroxylated fatty polyacids.

4. The cosmetic composition according to claim 1, wherein said anionic surfactant is present from 0.2% to 2% by weight relative to the total weight of the composition.

5. The cosmetic composition according to claim 1, wherein said lipophilic surfactant is present from 2% to 7% by weight relative to the total weight of the composition.

6. The cosmetic composition according to claim 1 wherein said anionic surfactant and said lipophilic surfactant are present according to an anionic surfactant/lipophilic surfactant mass ratio R of between 1/10 and 1/5.

7. The cosmetic composition according to claim 1, wherein the composition comprises at least one polysaccharide.

8. The cosmetic composition according to claim 7, wherein the polysaccharide is selected from the group consisting of scleroglucan gum, xanthan gum and derivatives thereof, guar gum, Lara gum, ghatti gum, sclerotium gum, starches, agar, agarose, carrageenans, lambda carrageenan and kappa carrageenan, carob flour, alginates, celluloses and derivatives thereof, hydroxypropylguar, pectins and gellan gum.

9. The cosmetic composition according to claim 7, wherein the polysaccharide is selected from the group consisting of a combination:
   scleroglucan gum and alginate,
   xanthan gum and alginate, and
   xanthan gum and guar gum.

10. The cosmetic composition according to claim 7, wherein the polysaccharide content is between 0.2% and 3% by weight, relative to the total weight of the composition.

11. The cosmetic composition according to claim 1, further comprising one or more oils, selected from the group consisting of plant oils, alkane oils and ester oils.

12. The cosmetic composition according to claim 1, further comprising one or more pigments having an average size by volume greater than 100 nm.

13. The cosmetic composition according to claim 1, further comprising one or more tillers, and/or one or more pearlizers.

14. The cosmetic composition according to claim 1, wherein the cosmetic composition further comprises at least one colorant.

15. A cosmetic composition having the form of an oil-in-water emulsion comprising:
   i) at least one lipophilic surfactant with HLB less than or equal to 9,
   (ii) at least one anionic surfactant comprising at least one group selected from the group consisting of (C6-C30) alkylsulfonates, (C6-C30)alkylamidesulfonates, (C6-C30)alkylarylsulfonates, alpha-olefin-sulfonates, paraffin-sulfonates, (C6-C30)alkylsulfoacetates, N-acyl (C6-C30)-N—(C1-C6)alkyltaurates, (C6-C30) acylisethionates, (C6-C30)alkylsulfolaurates, and salts thereof, and mixtures thereof;
   said composition comprising from 0% to 8% by weight of additional surfactant(s) relative to the total weight of the composition,
   wherein the cosmetic composition is stable after storage at 25° C. for one month and/or at 55° C. for 15 days, and
   wherein the additional surfactant(s), if present, do not comprise at least one nonionic surfactant.

16. The cosmetic composition according to claim 15, wherein the cosmetic composition further comprises at least one colorant.

17. A cosmetic treatment process for keratin materials, comprising applying the cosmetic composition as defined according to claim 1 to said keratin materials.

* * * * *